(12) United States Patent
Glukhov

(10) Patent No.: US 8,732,096 B1
(45) Date of Patent: May 20, 2014

(54) METHOD AND COMPUTER SYSTEM FOR MAKING OPTIMAL MEDICAL DECISIONS

(75) Inventor: Vacslav Glukhov, London (GB)

(73) Assignee: Vacslav Glukhov, London (GB)

( * ) Notice: Subject to any disclaimer, the term of this patent is extended or adjusted under 35 U.S.C. 154(b) by 284 days.

(21) Appl. No.: 13/329,245

(22) Filed: Dec. 17, 2011

(51) Int. Cl.
*G06F 15/18* (2006.01)

(52) U.S. Cl.
USPC .......................................................... 706/12

(58) Field of Classification Search
USPC .......................................................... 706/12
See application file for complete search history.

(56) References Cited

U.S. PATENT DOCUMENTS

| | | | |
|---|---|---|---|
| 6,687,685 B1 | 2/2004 | Sadeghi et al. | |
| 7,257,566 B2 | 8/2007 | Danielson et al. | |
| 7,426,474 B2 | 9/2008 | Schoenbaum et al. | |
| 7,809,585 B1 | 10/2010 | Ghouri | |
| 8,458,610 B2 * | 6/2013 | Kenney et al. | 715/771 |
| 8,566,115 B2 * | 10/2013 | Moore | 705/2 |
| 2010/0125462 A1 | 5/2010 | Aggarwal | |
| 2011/0016067 A1 | 1/2011 | Levchuk et al. | |

OTHER PUBLICATIONS

Arrow K.J: Uncertainty and welfare economics of medical care: The American Economic Review vol. 53: p. 941-973, 1963.
Commissioner Statement: FDA Commissioner Removes Breast Cancer Indication from Avastin Label Date: Nov. 18, 2011, http://www.fda.gov/NewsEvents/Newsroom/PressAnnouncements/ucm279485.htm , Decision of the Commissioner (PDF-4.4MB). Relevant information is the description of the decision making process and aggregate quantities used to arrive at the decision.

* cited by examiner

*Primary Examiner* — Michael B Holmes

(57) ABSTRACT

The present invention relates to a system and a method of making optimal medical decisions. In one embodiment presented for illustration the system comprises a quantitative model of the disease in the form of transition probabilities, the quantitative model of the effect of the medical treatment (therapy, drug or remedy) on the course of the disease, the quantitative model of costs and benefits, including monetary as well as non-monetary costs and benefits, and the model of preferences with respect to the costs and benefits. Using probabilistic inference, distributions of parameters of models are extracted from the data and the opinions of parties involved in the medical treatment. An expectation of the value of the treatment is computed. Optimality of the treatment is achieved by choosing the treatment or its parameters that give the greatest value given the evidence, the models, and the preferences. Other embodiments are discussed.

19 Claims, 9 Drawing Sheets

METHOD AND COMPUTER SYSTEM FOR MAKING OPTIMAL MEDICAL DECISIONS

CROSS-REFERENCE TO RELATED APPLICATIONS

Not Applicable

FEDERALLY SPONSORED RESEARCH

Not Applicable

BACKGROUND

Field of the Invention

This invention relates to the field of medical decision making, particularly to methods of optimal decision making and to automated systems providing for optimal medical decisions.

INTRODUCTION

The problem of the runaway growth of medical costs in developed countries has been recognized as one of the most important by economists and philosophers, medical professionals and politicians. Costs associated with various aspects of medical care are increasing both in absolute terms and as the fraction of the national product in developed countries.

Studies show that not all cost increases are medically justified ex post facto: for example, increase in spending is not always followed by the corresponding improvement in the survival rate. Various institutional and regulatory mechanisms have been implemented and are being considered to tackle the problem of the growth of medical costs. The power of institutional arrangements and regulatory acts to control costs is not certain. Considering the institutionalized diversity of political interests and ethical views, adoption of new regulations and the process of institutional change is difficult in modern society. Therefore, ethically and politically-neutral scientific and quantitative methods of making optimal medical decisions are in great demand.

Decision theory is the science of choosing in accordance with one's existing preferences and maximizing the satisfaction of one's values. From the standpoint of decision theory a medical decision is optimal if it is quantitatively justified in terms of values—in terms of benefits and costs, and if it is fair according to preferences for all parties involved. The invention I present provides a computer system and a method of making medical decisions which are optimal in this sense.

PRIOR ART

Considerable interest in computerized quantitative support of medical decisions exists for decades. Modern techniques include rule-based expert systems, neural network techniques, and probabilistic, also called Bayesian, methods.

A rule-based expert system is a collection of logical statements regarding patient conditions and possible treatments. Each statement is either true or false, and in the course of its operation the system arrives at a logical conclusion. The cause of the observed disease and the recommended treatment are derived from the rules. A rule-based system attempts to mimic the process of a rational thought. The drawbacks of this approach are its rigidity with respect to its internal logic, and its inability to use imprecise inputs.

Neural networks are based on the principle of reasoning where the model of the underlying process is unknown and needs to be inferred from the data. In a neural network the array of inputs representing the incoming information is connected to the array of outputs representing the decision. One or more layers of the so called inner nodes transform inputs into output by means of a mathematical model roughly matching the input-output characteristics of a mammal's neuron. Parameters of the model are established by a training algorithm which learns from the dataset of prior inputs and outputs. Neural networks work poorly in the situations where data sets are small, which is a commonplace in health care. Neural networks require the existence of a large set of desired outputs representing in the medical settings desirable outcomes. They cannot work in situations where non-data, such as opinions, are present.

Bayesian networks utilize probabilistic inference to arrive at a decision. A Bayesian network typically consists of nodes and connections between them. In the medical applications of Bayesian networks these nodes and connections represent the model of the disease. Nodes representing the probable causes, the conditions surrounding the individual, and the possible treatments. They are connected via implied causal links. Probabilities of the states of the nodes are inferred from the input data using the inference rules grounded in the theory of probabilities. Probabilistic inference utilized in Bayesian networks is a powerful quantitative tool. It can combine data and non-data such as opinions.

Probabilistic inference is central in in U.S. Pat. No. 7,809,585 to Ghouri. In this patent the costs of the medical decision are introduced in the context of administering a particular treatment. This invention belongs to the class of the rule-based systems wherein the suggested treatment is the result of a chain of logical statements regarding the patient's conditions and different treatments. Probabilistic inference is used to determine that the treatment will be effective given that the patient has the disease. However, studies show that for a single diagnosis several different treatments can be proposed. These treatment can vary in terms of their effectiveness and risks: they can have different probabilities of success, different complications, different length and vastly different costs. The system disclosed in the invention in Ghouri therefore does not address the problem of optimization of medical costs and benefits and does not address the fact that different parties involved in the medical decision such as the patient and the provider, always have different preferences with respect to risks and probable costs. The system disclosed in Ghouri does not address the issue of optimality of the treatment under the constraints and preferences of parties involved either. The system disclosed in Ghouri therefore cannot be used as a support system for the optimal medical decision making.

Another computerized system to automate medical decision making is described in U.S. Pat. No. 6,687,685 to Sadeghi et al. The patent discloses a Bayesian network system. Conditional probabilities in the network are adjusted in real-time as new evidence is supplied. The evidence comes in the form of answers to questions comprising a dynamic set designed to identify a diagnosis or the patient's conditions. When all questions are answered, one node of the network contains probabilities of different causes. At this point the invention disclosed in Sadeghi introduces the concept of the utility nodes. Utility of the decision is supplied by the institution responsible for operating the system is given in arbitrary units, called "utils". The objective of the method in Sadeghi et al is to ensure that the correct decision has the greatest utility. The critically important for the cost control problem remains, however, unsolved by Sadeghi et al. In real applications, however, medical practitioners and patients alike are concerned with making optimal medical decisions taking into account probable actual costs and probable actual benefits. In every medical case many correct decisions are possible given the evidence. This fact is so well known in the industry and by every patient that it has been popularized and epitomized by the now famous TV series "House, M.D.": the drama of the optimal decision making in healthcare is to find the best decision among many possible correct decisions given the evidence and the uncertainty of the consequences of treatments. The invention disclosed in Sadeghi does not address this problem.

SUMMARY

None of the previous approaches explicitly addresses the problem of the optimal cost-effective choice of treatment in the presence of the uncertainty of outcomes of treatments. None of the earlier solutions presents a solution in the situations where cost preferences of different parties are taken into account in the decision making process.

The object of this invention is to present the solution to such problems in the health care industry where the optimization of costs is required in the presence of complex and imprecise information about the disease, about the effectiveness of the treatments of the disease, and about the costs associated with and arising from the treatments.

It is a further object of the invention to present a specific quantitative method capable of explicitly accounting for the uncertainty of data and for the model risk in the problem of making optimal medical decisions.

It is a further object of the invention to present a method of representation of a disease, treatments, benefits and costs that permits optimization of medical costs and benefits.

It is a further object of the invention to present a computerized system configured to perform computational tasks necessary to make an optimal medical decision.

It is a further object of the invention to present a method of making optimal medical decisions agreeable to all parties involved in the care of the patient.

DETAILED DESCRIPTION

Detailed Description: Introduction

I will now describe the first embodiment of the invention. I will start from the general description of computing modules included in the first embodiment, their linkage and the flow of information leading to the optimal medical decision and to the actions of the parties involved. I will describe the models and the quantitative methods included in the first embodiment. I will conclude with the description of the general operation of the system, and with a concrete application of the system. Finally, I will discuss other embodiments and possible ramifications, and the advantages of the invention.

For the purpose of discussion, this description will focus on a computer system comprising computing modules, data storage units, and computerized data entry units. A person skilled in the art is able to recognize that the discussion herein will apply equally to a fully autonomous system in which all computing modules are combined into a single physical system, such as personal computer, a tablet, a palmtop computer, a smartphone, or a specialized device capable of performing computing and data input, output and display operations specified herein.

For the purpose of discussion, this description will focus on a method of making optimal medical decisions comprising several steps specified as particular mathematical procedures. This description will also focus on probabilistic models in their particular functional forms. These explicit mathematical procedures describe specific models of the underlying processes only for illustrative purposes. A person skilled in the art is able to recognize that the method discussed herein will apply equally to mathematical procedures comprising differing number of steps and differing models of the underlying processes.

The computer systems and the methods of the invention make extensive use of probabilistic inference. By probabilistic inference I mean mathematical methods and algorithms of evaluating probabilities of models of processes and probabilities of their parameters. Probabilistic inference is based on models which are assumptions about the underlying processes, and on the observable data. The ultimate goal of probabilistic inference is to compute expectations of uncertain quantities and to make predictions of outcomes of future events based on the assumptions and the data. A person skilled in the art possesses the knowledge of the methods and the algorithms of probabilistic inference and is able to implement the required methods and algorithms of probabilistic inference discussed herein.

Figure 1:
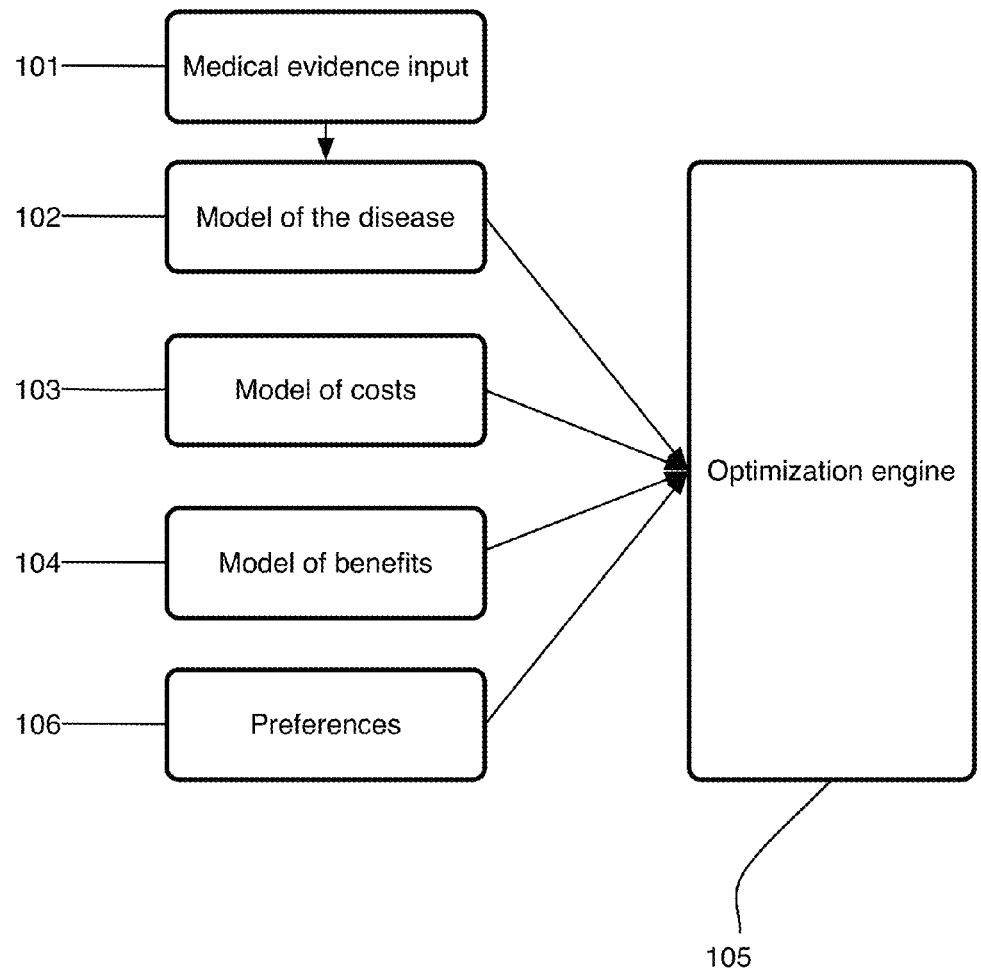
FIG. 1 is a flowchart showing basic elements of the system and the flow of information between them.

As I show in FIG. 1, the computing system for making optimal medical decisions comprises a medical evidence entry module 101; a computing module 102 configured to perform calculations necessary to operate a model of the disease comprising a medical evidence model and a model of the treatment; a computing module configured to operate a model of costs 103; a computing module configured to operate a model of the benefits 104; a parameter entry and computing module configured to operate a model of individual preferences 106; and an optimization computing module 105.

Computing modules and input modules are configured to receive the input data and to pass the results of their computations using standard electronic data communication interfaces commonly used to pass data and instructions. These interfaces include, but not limited to, direct memory data transfer, serial port communication devices and protocols, universal serial bus devices and protocols, and infrared, wireless or wired network hardware and software.

In the following sections I will discuss how in the first embodiment of the invention the modules are connected, and how they are configured to perform the steps of the method leading to the optimal decision.

Computing Module for the Model of the Disease

I will now discuss the central element of the first embodiment of the invention, the computing module for the model of the disease, its connections to other modules, and details of the model of the disease.

The model of the disease resides in the computing module 102 which comprises a computing processor and a data storage. The computing module is configured to perform probabilistic inference using the data and the model of the disease stored in the data storage, and to pass the results of the computations to the optimization engine computing module 105. The computing module 102 is configured to perform probabilistic inference of possible medical conditions or possible states of a disease given the medical evidence supplied by the medical evidence entry module 101. The method of the probabilistic inference, which the computing module 102 is configured to apply, is described in the section entitled "Model of the disease: Method for the probabilistic inference of the state of the disease".

Medical States

The model of the disease comprises of one or more medical states representing a healthy individual and one or more medical states representing a diseased individual.

The patient in one of the medical states in the next period of time can remain in the same condition with some probability or transition into another condition with some probability. The probabilities of staying in the initial medical state or transitioning into another medical condition depend on many factors and are affected by the patient's treatment.

The first embodiment's model of the disease comprises medical states and the probabilities of transitions between them. The model comprising states of the disease embodies essentials of the body of knowledge related to the disease. It is suitable for the methods and the algorithms of probabilistic inference.

A healthy individual is a commonly recognized medical state which can be detected by the set of facts comprising a normal body temperature, ranges of normal heartbeat and breath rates, the absence of inflammation, a range of the red blood cell count, cholesterol count, and by other medical facts and their combinations deemed essential in a healthy individual. The state of a healthy individual is easily extended to include pertaining medical facts such as the individual's lifestyle and the environmental conditions.

Figure 2:
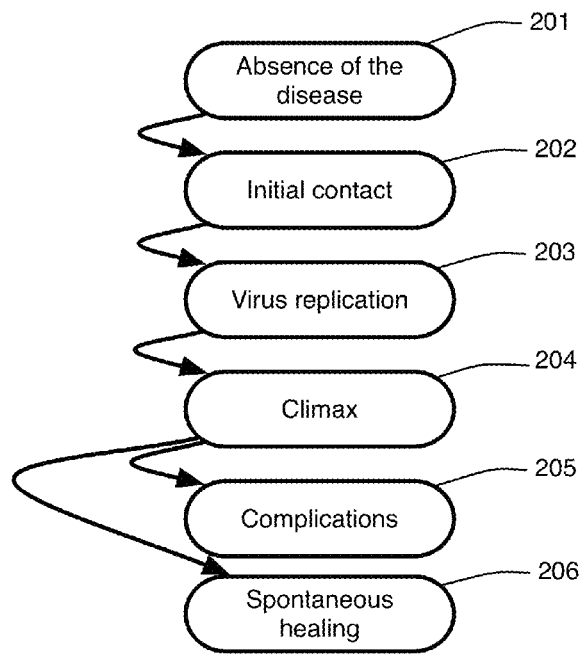
FIG. 2 is a flowchart showing the set of distinct states of a disease and transitions between them using the example of the common cold.

The model of the disease also includes one or more states of the disease. These states are linked by the progression of the disease, or, in other words, by its temporal development. For example, I show in FIG. 2 that the natural course of the common cold can be modeled as a set of medical conditions: the medical condition of a healthy individual 201, transitioning consecutively into the initial contact state 202, the onset of the virus replication state 203, the climax 204, a set of possible complications (205), and the state of spontaneous healing 206.

Distinct features of states of a particular disease are defined by the body of contemporaneous knowledge and by the medical opinions pertaining to the disease's nature and progression. This knowledge is necessarily imprecise and the opinions are necessarily subjective.

Medical Evidence

Medical states are seldom directly observable or measurable. Instead, directly observable or measurable is medical evidence.

In the first embodiment the medical evidence is supplied via the medical evidence data entry module 101. For the purposes of the manual input, the module 101 comprises a computer terminal such as a personal computer configured to display an entry form. The entry form presents the set of medical facts possibly pertaining to the patient. For the purposes of the automated data input, the data are supplied by a device such as a blood pressure monitor, a heartbeat monitor, or a temperature measurement device. These data entry devices are connected to the medical evidence module to collect automatically and in real time the medical facts pertaining to the disease.

Natural Progression of the Disease and the Effects of the Treatment

In the first embodiment the model of the disease further comprises the model of the possible future progression of the disease. This model is represented by probabilities which specify the chances with which the disease progresses into other conditions or states within certain time interval given that the current medical condition is established with certainty.

Figure 5A:
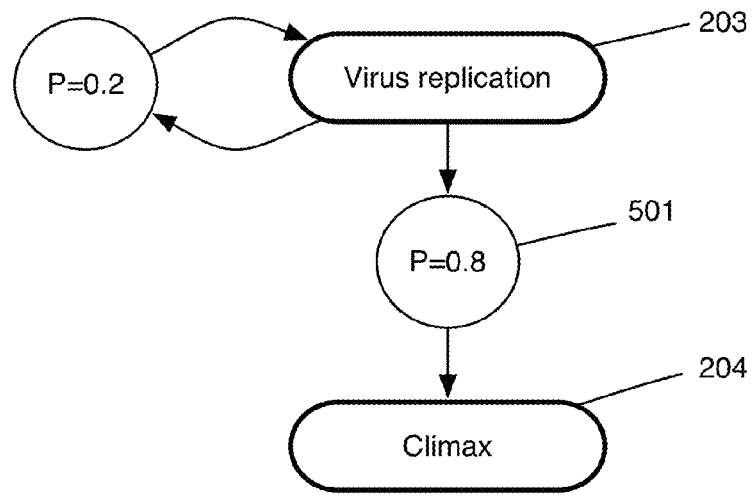
FIG. 5A is a state diagram showing the natural progression of a disease using the example of the common cold and the two distinct states of the disease.

For example, if it is established that the patient suffers from the common cold and it is established that the disease is in the virus replication stage, then it is known with almost certainty that within several days the disease will progress into the climax. FIG. 5A illustrates the statement that without any treatment the common cold progresses into the climax within 3 days from the replication state with probability 80%. That is, $$P(\text{Climax}, t+3 \text{ days} | \text{Replication}, t) = 0.8.$$

Such probabilistic statement linking two states of the disease separated by time is called a transition probability. The transition probability 501 is stored in the model of the disease. I will describe the computation of transition probabilities in the first embodiment of the invention in the section entitled "Model of the disease: Method for probabilistic inference of transition probabilities".

The objective of a treatment is to alter the natural progression of the disease. The outcome of the treatment is never certain. In the model of the disease the effect of the treatment is expressed as a probability distribution.

Figure 5B:
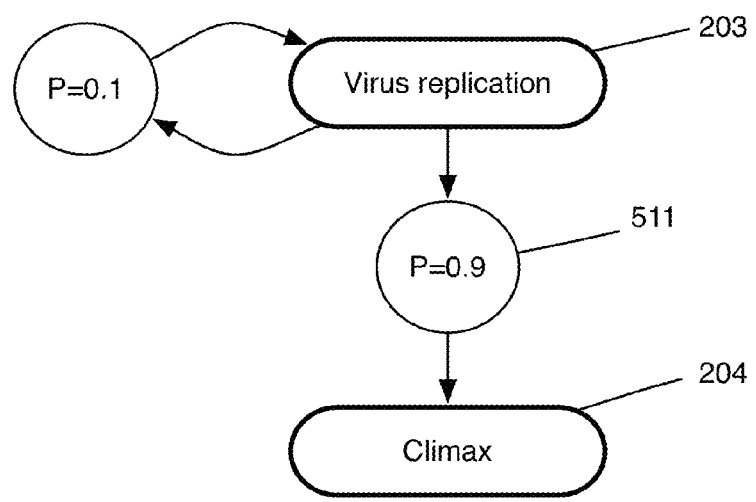
FIG. 5B is a state diagram showing the progression of a disease altered by a treatment using the example of the common cold and the two distinct states of the disease.

For example, according to the current body of knowledge related to the common cold, no known remedy reliably alters the average duration of the disease from the onset to the spontaneous healing. However, various remedies are known to affect the progression of the disease with some probability. FIG. 5B demonstrates how the treatment alters the course of the disease by changing the transition probability. In FIG. 5B the treatment is applied and there is less chance to stay in the virus replication, so that the disease progresses quicker to the next stage. The new transition probability assignable to the treatment, shown in FIG. 5B as 511, is computed as described in the section entitled "Method for probabilistic inference of multiple transition probabilities" and is stored in the data storage.

Any treatment carries risks. The risk of the treatment may include various complications, unwanted side effects, and even the onset of a different disease. For example, it is known that such a common cold remedy as ibuprofen carries the risk of nausea, and, infrequently, of heart failure. In the first embodiment of the invention the model of treatments of the disease includes probabilities of known complications and side effects.

The model of the disease thus comprises the medical facts about the medical conditions or states of the disease in the form of the evidence, the transition probabilities, and the effect of treatments on the transition probabilities.

The model of the disease represents the state of knowledge about the nature of the disease and encapsulates all available data and medical opinions about the progression of the disease and the outcomes of treatments. New medical facts, data and opinions are added as they become available and all models and are recalculated and probabilities are reevaluated.

Model of the Disease

Method for the Probabilistic Inference of the State of the Disease

Probability of the State of the Disease Given the Evidence

In the first embodiment of the invention the state of the disease is probabilistically inferred from the medical evidence. The method of probabilistic inference uses the model of the causal relationship between the state of the disease and the evidence. The probable state of the disease being S, the medical evidence being E, the probability of S given the evidence E is computed according to the probabilistic chain rule, also called Bayes' Theorem:

$$P(S \mid E) = \frac{P(E \mid S)P(S)}{P(E)}$$

For example, if the evidence E always observed when the state is S, then $P(E|S)=1$ and the probability of the state given the evidence is just the ratio $P(S)/P(E)$. On the other hand, if the evidence E is not linked to the disease S, the probability of the state S given the evidence E is simply equal to the probability of the state $P(S|E)=P(S)$. In this case there is no new information given by the evidence E: one says that the evidence E is not informative. Some types of evidence are only weakly informative. An example of a weakly informative evidence is as follows. Suppose a genetic test shows that 99 percent of all autistic children exhibit certain genetic feature E, whereas only 1 percent or non-autistic children do. Suppose further that the probability of a child being autistic $P(S)=0.001$. From the probabilistic inference formula it then follows that a child tested positive for E has approximately $P(S|E)=0.99*0.001/0.01=0.099$ or approximately 10% chance of being autistic. The weak evidence for autism can be strengthened or weakened when combined with other independent evidence E1, E2 and so on. In the first embodiment of the invention there is no pre-determined threshold which separates non-informative evidence from the informative evidence. The first embodiment of the invention is configured to implement the principle that no information is to be thrown away without a specific reason: the system is generally configured to accept a very weak evidence as well as very strong evidence for the disease. However, for practical purposes, the system is also configured to ignore the evidence if it points to the probability of the state of the disease less than a certain parameter, for example, $10^{-10}$. This parameter is configurable by the user.

The causal relationship between the evidence and the state of the disease is a part of the model of the disease. The data necessary to estimate probabilities in the expression above are provided by the observations of the incidence of the evidence E, and by the incidence of the state of the disease S, and by the proven incidences of the state S causing the observable evidence E.

Probability of the State of the Disease Given the Evidence and Prior Information Prior information I, sometimes called "beliefs" in probabilistic inference, enters the calculation in the following form:

$$P(S \mid EI) = \frac{P(E \mid SI)P(S)}{P(E \mid I)}$$

Through this computational method, prior information, such as doctor's opinions, denoted by I, is included into the computation of the probability of the state of the disease.

For example, the doctor can include some vague non-data into the decision making process. Such non-data can be supplied as a statement by the patient or his or her relatives. For example, the fact for a particular individual vomiting is frequently associated with migraine, but not necessarily with the common cold, can serve an opinion I which gives the evidence E—vomiting—more preference toward migraine-related diseases rather than toward the common cold.

Figure 3:
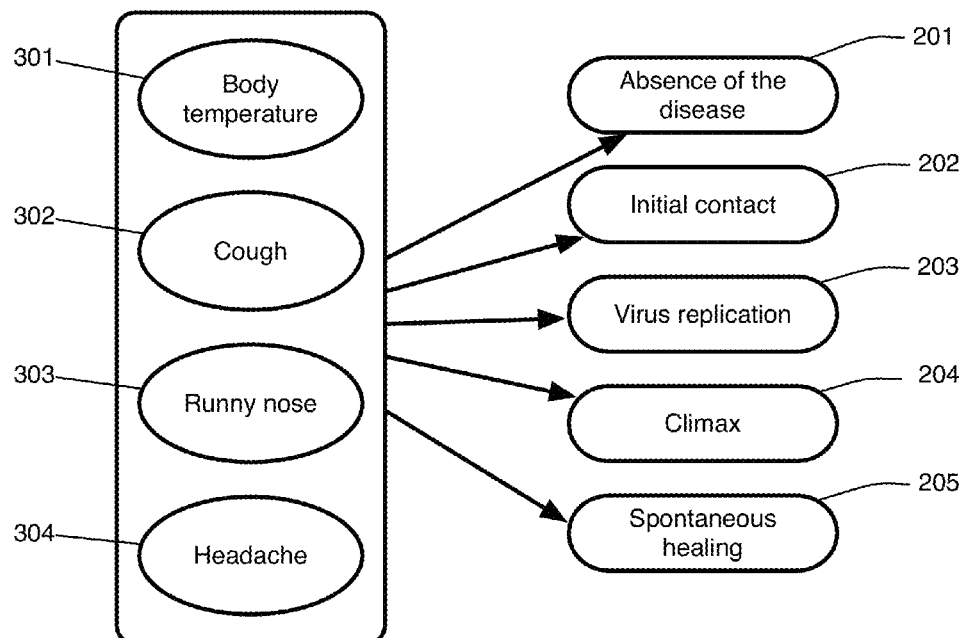
FIG. 3 is a chart showing how the medical evidence represented by the set of symptoms can point to different states of a disease using the example of the common cold.

Medical evidence comprises one or several medical facts. A medical fact is a medical sign, a datum, a symptom, or their combination. For example, an elevated body temperature is the symptom for the common cold representing one of the mechanisms of the body response to the viral infection, which in itself is difficult or impossible to observe or measure directly. As I show in FIG. 3, in the model of the common cold, evidence is the combination of elevated body temperature 301, along with other medical facts, such as cough 302, runny nose 303, headache 304, and so on. When the state of the disease is directly measurable, the measurement of the state is its evidence pointing to it with certainty. Directly measured concentration of viral particles of a certain kind in the patient's bloodstream is a directly measurable evidence of the common cold.

Figure 4:
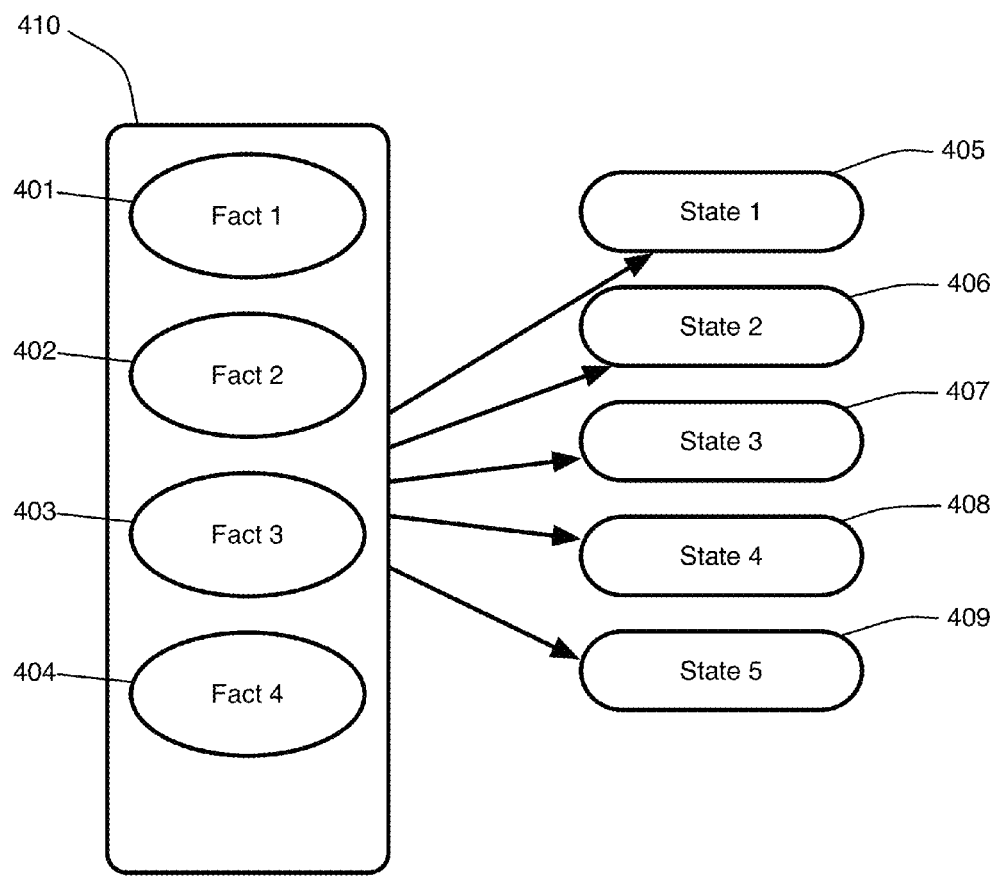
FIG. 4 is a chart showing how the medical evidence represented by the set of facts can point to different medical conditions.

In FIG. 4 I show the general scheme where the medical evidence 410 comprising the following elements: Fact 1 (401), Fact 2 (402), Fact 3 (403), Fact 4 (404), is probabilistically linked with the states of the disease. The evidence can point to different medical conditions or states of the disease— to the State 1 (405), State 2 (406), and so on, with different probabilities. A probabilistic statement which specifies the probability of a certain state given the evidence E is P(S|E). For the example of FIG. 4, probability of the State 1 denoted by $S_1$ is given by $P(S_1|F_1F_2F_3F_4)$.

An Example of the Simple Evidence E and the State S

For the illustrative purposes, I will now discuss how the probabilities of states of the disease are computed in the first embodiment of the invention for one simple case.

In the first embodiment this probability is represented by a probability distribution. For example, if the medical data indicate that out of N patients exhibiting the evidence E exactly M were found to have the medical condition S, then the possible distribution of the probability P(S|E) is represented by the following Beta distribution: □ □ □

$$p = P(S|E, M, N) \sim \frac{\Gamma(N+2)}{\Gamma(M+1)\Gamma(N-M+1)} p^M (1-p)^{N-M}$$

According to this distribution that I use in the first embodiment of the invention, the most likely probability $p_{max}$=M/N equal to the intuitive understanding of the probability of the state of the disease. In the first embodiment this probability along with the width of the distribution is displayed to the user for reference purposes.

I will discuss other examples of probability distributions in other sections.

In the second embodiment, the system is configured to use a Bayesian network representing a system of causal relationships between medical conditions and the evidence. The Bayesian network outputs the probability of a directly unobservable condition, given the evidence on hand. Such Bayesian networks are normally used as a diagnostic tool typically presenting to the user the most probable diagnosis. Contrary to the traditional use, in the second embodiment of the present invention the Bayesian network of causal relationships is the part of the model of the disease and outputs probabilities of all possible diagnoses. The method of calculations and the output of the model in the case of a Bayesian Network is substantially similar to the procedure of simple probabilistic inference.

Model of the Disease

Method for Probabilistic Inference of Transition Probabilities

Future States Given the Evidence

In the first embodiment of the invention the model of the disease is employed whereby the disease progresses from one state or medical condition to another governed by transition probabilities. The purpose of a medical decision is to alter the probable natural progression of the disease in such a way that it will benefit the patient.

In the first embodiment of the invention the probable natural progression of the disease, given the evidence E, is computed using the following method: □ □

$$P(S_1|E) = \sum_{S_0} P(S_1|S_0)P(S_0|E)$$

The transition probability □ □

$$P(S_1|S_0)$$

is the probability that the initial state □ □ □

$$S_0$$

will transition to the new state □ □

$$S_1$$

in the next period.

The effect of the treatment is uncertain for the following two reasons. First, given the evidence E the initial state of the disease is uncertain. Second, given the treatment and the state of the disease, the outcome is uncertain as well. The effect of the treatment, given the evidence, is computed using the following formula: □ □

$$P(S_1|E) = \sum_{S_0} P(S_1|TS_0)P(S_0|E)$$

The transition probability □ □

$$P(S_1|TS_0)$$

is the probability that the initial state $S_0$ will change to the new state $S_1$ in the next period if the treatment T is applied.

In the first embodiment the expected values $E(P(S_1|TE))$ and $E(P(S_1|E))$ of the next state probabilities $P(S_1|TE)$ and $P(S_1|TE)$, respectively, are displayed to the user for informative purposes. User of the system of the invention, however, is also made aware that these expectation values are only intermediate results of the decision making process. The user is informed that the true prognosis of the progression of the disease, given the treatment T, is described by a distribution of the probability.

I will now describe how the transition probabilities are modeled in the first embodiment.

Probabilistic Description of Transitions Via a Multiparametric Distribution

Given the medical condition, probabilities of staying in it or transitioning into other states of the disease or other medical conditions are not independent. In the first embodiment they are modeled as the multi-parameter distribution of probabilities.

Parameters of multi-parameter distributions of probabilities are evaluated using the technique similar to that described in the section entitled "Model of the disease: Method for the probabilistic inference of the state of the disease". The distribution of transition probabilities given a certain initial state of the disease is described by the Dirichlet distribution with the vector parameter $\alpha=\{\alpha_1, \alpha_2, \ldots, \alpha_k, \ldots\}$ □ □. For example, transition probabilities from State 1 of FIG. 4 $p_{1i}=P(S_i|S_1)=1 \ldots 4$, are distributed according to $$\{p_{11}, p_{12}, p_{13}, p_{14}\} \sim \frac{\prod_{i=1}^{4} p_{1i}^{\alpha_i}}{B(\alpha)}$$

where $$B(\alpha)) = \frac{\prod_{i=1}^{4} \Gamma(\alpha_i)}{\Gamma\left(\sum_{i=1}^{4} \alpha_i\right)}$$

In the illustrative case above the medical data are represented by the histogram of observations of past transitions.

In the first embodiment of the invention the prior beliefs and the medical opinions are introduced as additive parameters $\alpha_{0i}$ of the corresponding Dirichlet distribution in the manner similar to that described in the previous section. The set of medical data $\alpha_i$ and medical opinions $\alpha_{0i}$ along with the Dirichlet model of the transition probabilities in the model of the disease accounts for all available data and knowledge about the progression of the disease.

The data are stored in the vector $\alpha = \{\alpha_1, \ldots, \alpha_4\}$. Distributions of transition probabilities are thus fully defined by the stored vectors of $\alpha$, $\alpha_0$—for the natural, or the baseline progression of the disease, and the stored vectors of $\alpha(T_k)$, $\alpha_0(T_k)$, $T_k=1 \ldots K$—for various treatments $T_k$ The model of the disease described in the previous sections as the part of the first embodiment of the invention is the first and the only system capable of making use of these data.

This concludes the description of the model of the disease.

Computing Modules for the Models of Costs and Benefits

The Models of Costs

The model of costs resides in a computing module 103 comprising a computer processor and a data storage. The computing module is configured to perform probabilistic inference of probabilities of costs associated with medical conditions and costs associated with medical decisions. This system is capable of outputting the results of the inference calculations and passing them to the optimization engine 105.

There are several distinct bearers of costs associated with a medical condition and the corresponding models of costs. These are the costs borne by the patient, the costs borne by the provider, and the costs borne by the society. Patient's costs include costs associated with pain, suffering, lost productivity, or lost income due to the chance of premature death, and other uncertain costs. Provider's costs comprise direct costs of implementing a medical decision, costs associated with providing medical care under such or another medical condition, and other uncertain costs. The social costs include the costs associated with the chance of spreading the disease among a larger population, if the disease is transmittable. Since the ultimate size of the population affected by the disease due to it being contagious is uncertain, the corresponding social costs are uncertain as well.

Costs associated with a medical condition or a state of the disease are modeled as probabilistic distributions given the state of the disease.

Figure 7:
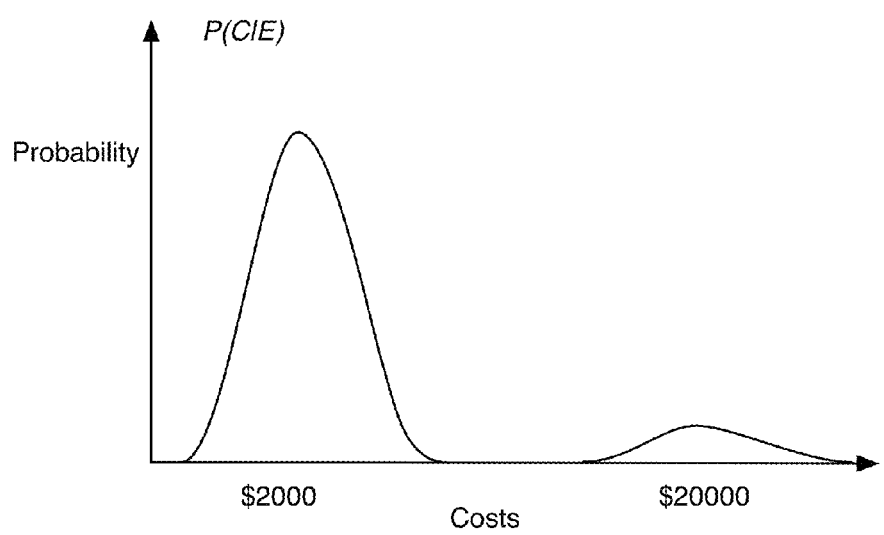
FIG. 7 is a illustrative graph of the probability distribution of costs showing two concentrations near $2000 and near $200000.

Costs associated with the medical decision or the treatment are modeled as probabilistic distributions given the state of the disease S and the treatment meant to be applied T. For example, if the evidence E indicates that the patient suffers from the disease A with high certainty, but the same evidence indicates that the patient may also suffer from the disease B with some small probability. The most effective treatment for the disease A is T1 and for the disease B is T2. However, if the actual disease is B and the treatment is T1, then additional, possibly large, costs may arise due to the treatment T1 applied to the patient suffering from the wrong disease. In this case, given the medical evidence E and the proposed treatment T, the distribution of costs P(C|E,T1) might resemble that shown in FIG. 7. In this FIG. 1 show an example of the cost distribution where the bulk of the probability of costs, associated with the correct treatment, is concentrated around $2000: these are the costs associated with the treatment T1 when the disease is indeed A. However, there is a small chance of cost being around or exceeding $20000, when the disease B is treated with T1.

Typically, situations like the one in the example above are handled by insurance. However, some costs are not insurable, especially in the area of unique or rare treatments, conditions and decisions. The process of medical innovation such as the emergence of experimental and innovative treatments is also characterized by uninsurable and highly uncertain costs. Some costs are not insurable because the insurance costs are prohibitively high. The first embodiment of the invention makes use of explicit probabilistic distributions of costs. It incorporates these distributions of costs into the decision making process, making the optimal medical decision informed.

In the first embodiment of the invention the model of costs comprises the model of the individual costs and the model of the provider costs.

The computing module 103 is configured to perform probabilistic inference both for the monetized costs and for the non-monetized costs. Monetized costs are expressed in the same currency units. This allows costs of differing nature to be compounded and compared arithmetically. Non-monetized costs exist in the form of a logical or probabilistic statement and are characterized by the magnitude of its effect and by its probability.

An example of non-monetized costs is reputation. An occurrence of obstetrical death negatively contributes to the reputation of the health care provider. Costs similar to the reputation costs generally cannot be expressed in the monetary form. In the first embodiment of the invention non-monetized costs are compared and compounded with other non-monetized costs of the same nature. For example, the probability of obstetrical death can be compounded with other possible causes of death during the treatment. The compounded death rate distribution, which then becomes the distribution of non-monetized costs for the treatment under consideration, is then probabilistically inferred by the computing module 103 from the original distributions of different types of death rates. In the first embodiment of the invention the computing module 103 is configured to perform probabilistic inference for many possible types of non-monetized costs. The models of these costs are stored in the form of probability distributions.

The Model of Benefits

The model of the benefits 104 resides in a computing module comprising a computer processor and a data storage. The computing module is configured to perform probabilistic inference of probabilities of benefits associated with medical decisions. This system is capable of outputting the results of the inference calculations and of passing them to the optimization engine 105.

In the first embodiment the model of the benefits includes the monetized and non-monetized positive outcomes of the treatment which are not trivially included in the model of costs described in the previous section. As an example, a non-trivial model of benefits include the uncertain benefits of the treatment of a terminally ill patient when such treatment only prolongs some of the patients' lifespan, but does not alter substantially the aggregate rate of survival. Currently, if a treatment does not significantly and positively affect the aggregate rate of survival, the treatment is typically rejected by the regulatory body. For example, this was the sole reason why the treatment of certain types of cancer with the drug Avastin has been rejected by the regulatory body in the United States. Contrary to the current practice relying exclusively on aggregate quantities such as the survival rate, the first embodiment of the invention permits making individually optimal medical decisions based on probabilities of differing outcomes and probabilities of differing benefits. The optimal decision based on benefits defined for an individual patient or a group of patients, for an individual provider or a group of providers, is more informed, is more justified, is fairer, and therefore is better.

Method of the Computation of Distributions of Benefits (or Costs Savings) of the Treatment In the first embodiment the probabilistic distribution of the benefits B of the treatment T is represented by the distribution of costs given the treatment adjusted for the average costs in the absence of the treatment. □ □ □ □

$$P(B|TE)=P(B+E(C|E)|TE)$$

Figure 8:
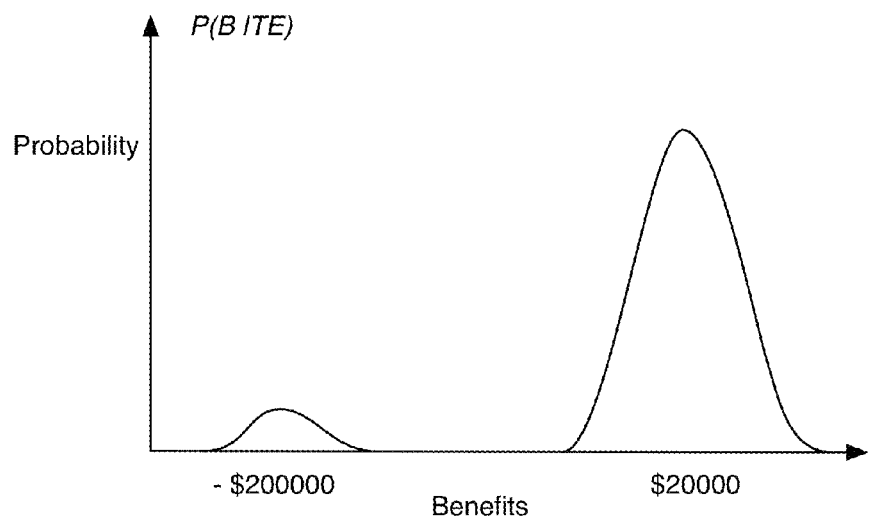
FIG. 8 is an illustrative graph of the probability distribution of benefits of a treatment showing two concentrations near $20000 and near the negative −$200000.

Probabilistic distribution of the benefits of the treatment is not necessarily concentrated in the positive domain B>0 □ □. For example, if there is a probability that given the evidence E the treatment T is wrong for the actual and directly not observable state of the disease S, the distribution of the benefits of the treatment contains a hump in the negative domain indicating the costs associated with the wrong treatment. In FIG. 8 I show an example of the situation when the bulk of the distribution of benefits of a treatment is positive and is concentrated around \$20,000. At the same time in FIG. 8 there is a small probability of negative benefits shown as a hump around the value of −\$200,000. This part of the cost distribution is associated with a small probability of the actual medical state being different from that for which T is most appropriate.

The first embodiment of the invention the module 103 computes the distribution of the effects of the medical decision according to the current state of knowledge about the disease. The distribution of the effects of the medical decision depends on the probability of being in a certain state of the disease after the treatment. As the model of the disease and the effects of the treatment are updated, so are the transition probabilities and the benefit functions.

Method for the Computation of Distributions of Costs and of Functions of Costs Given the evidence, the state of the disease is uncertain and so is the distribution of costs. In the first embodiment the probability distribution of current costs is calculated as follows: □ □

$$P(C|E) = \sum_S P(C|SE)P(S|E)$$

Similarly, if the evidence E, the prior opinions I, and the treatment T are given, the probable distribution of costs is calculated as □ □

$$P(C|EIT) = \sum_S P(C|SEIT)P(S|EIT)$$

The expected value X of the function of costs F(C) given the evidence, opinions and the treatment is computed according to the following method □ □ □ □

$$X(f(C), EIT) = \sum_C F(C)P(C|EIT) = \sum_C F(C) \sum_S P(C|SEIT)P(S|EIT)$$

In this expression the function of costs is averaged over the distribution of costs given the evidence, opinions, and the treatment, which in turn is computed with the probabilities of various costs in possible states.

A function of costs may in turn include the probability of costs as one of its arguments. In this case computations are becoming □ □ □

$$X(F(C, P(C), EIT)) = \sum_C F(C, P(C))P(C|EIT)$$

The function of costs that depends on the probability of costs is used to exclude highly improbable states. In the first embodiment of the invention a cut-off parameter configures the system to exclude extremely improbable costs arising, for example, from an extremely exotic combination of complications. The cut-off parameter is the property of the function of costs. In the first embodiment of the invention a piecewise linear function of costs is used to calculate the costs expectance over the distribution of costs: □ □ □

$$L(C, P(C)) = \begin{cases} C, & P(C) \geq P_{cutoff} \\ C_{cutoff}, & P(C) < P_{cutoff} \end{cases}$$

In this function those costs which are associated with extremely improbable outcomes are folded into the cutoff costs constant and the cutoff probability constant. Both are configured by the user of the system.

Method for the Representation of Uncertainty Associated with Imprecise Knowledge In the first embodiment of the invention the following method is used to quantify the lack of precision associated with the imprecise character of the models. In the computing module for the model of the disease 102, the computing module for the model of costs 103, and in the computing module for the model of benefits 104 uncertain probabilities in the models are represented in the functional form of distributions of probabilities. One of such distributions was presented in the previous section as the distribution of p=P(S|E), the probability of the medical condition S given the evidence E.

Probabilistic inference operates with the data present in the system. The first embodiment also includes the possibility of using prior beliefs or opinions in the distribution. The full distribution of the probability p=P(S|EI) of the medical condition S given the evidence E and the prior beliefs I is expressed in the form of the so-called Beta distribution:

$$B(p; \alpha, \beta) = \frac{\Gamma(\alpha+\beta)}{\Gamma(\alpha)\Gamma(\beta)} p^{\alpha-1}(1-p)^{\beta-1}$$

Parameters $\alpha$ and $\beta$ of the Beta distribution are the parameters of the model of the probability P(S|EI).

The estimates of the parameters that take into account prior beliefs are obtained as follows:

$$\alpha = M + \alpha_0$$

$$\beta = N - M + \beta_0$$

where N is the total number of events and M is the number of the events for which the distribution of probability is being estimated and the parameters with the zero subscript denote the prior beliefs contained in the system and/or supplied by the user.

In the first embodiment of the invention all integration and summation over distributions of probability is performed on the optimization stage in the optimization module 105. In the following sections integration and summation over the distributions of probability are omitted for the sake of simplicity of the discussion. A person skilled in the art understands that integration over the probabilities is performed whenever uncertain probabilities are present.

Computing Module for the Model of Individual Preferences

In this section I will discuss how the module for the individual preferences 106 is configured to compute and pass to the optimization module 105 the values of functions of individual preferences.

In the first embodiment of the invention preferences of individual participants are the integral part of the optimal decision making process. They reflect the fact that given the same evidence and the same model of the disease and the same state of knowledge about the models, the optimal medical decision is different for differing individuals and providers.

For example, some individuals are willing to tolerate more risk than other individuals. These patients are more willing to choose an experimental treatment, and more willing to offer themselves as subjects of medical trials than other individuals. Optimal medical decisions and treatments for this group of patients are different from the optimal decisions and treatments for more conservative patients.

Similarly, for example, a medical institution, whose recovery and mortality statistics is for some reason below the average, might be reluctant to select a potentially more effective treatment carrying more risk than a medical institution whose statistics is above the average.

The first embodiment of the invention permits the quantification of these preferences using functions of individual preferences.

The individual preferences are represented by a function of costs, benefits, and their probabilities F called the utility function. The function maps each combination of costs, benefits and their probabilities to a number in such a way that all combinations of costs, benefits and their probabilities are ranked: a better combination of costs, benefits and their probabilities corresponds to a greater value.

The first embodiment of the invention configured to use the following individual utility function types.

The computing module for the individual preferences 106 is configured to utilize a standard constant absolute risk aversion (CARA) utility function which is programmed as follows:

$$F_{CARA}(C, \eta) = \eta\left(1 - e^{-\frac{C}{\eta}}\right)$$

In this formula and thereafter the monetary value of costs is assumed negative, so that the utility function F decreases with C as C tends to greater negative values. In the CARA function the individual preferences are expressed by the risk aversion parameter $\eta$ which represents the party's level of tolerance of risks in the same terms (monetary or not) in which the numerator C is expressed. For example, if the costs C are computed in the amount of US dollars, the risk aversion parameter is equal to the risk tolerance in US dollars as well. Similarly, if the costs are computed in the non-monetary form of the mortality rate, the risk tolerance parameter is proportional to the tolerable mortality rate as well. The risk aversion parameter is entered in the module 106 by the user of the system according to the user's preferences.

The second type of the utility function included in the first embodiment is the cost-cutoff function.

$$F_{cutoff}(C, \eta = C_{cutoff}) = \begin{cases} C, & C < -|C_{cutoff}| \\ 0, & C \geq -|C_{cutoff}| \end{cases}$$

Integrated over the distribution of costs the cutoff function gives the average expected cost exceeding certain value. The cutoff value is configured by the user according to the user's preferences.

The third type of the utility function, which is provided in the first embodiment, is represented as an integral over the probabilistic distribution of costs. A person skilled in the art will recognize it as a standard percentile function:

$$F_{\%C}(C = R, \eta = \%C) = \arg_R \int_{-\infty}^{R} P(C|\ldots) dC = \%C$$

Figure 9:
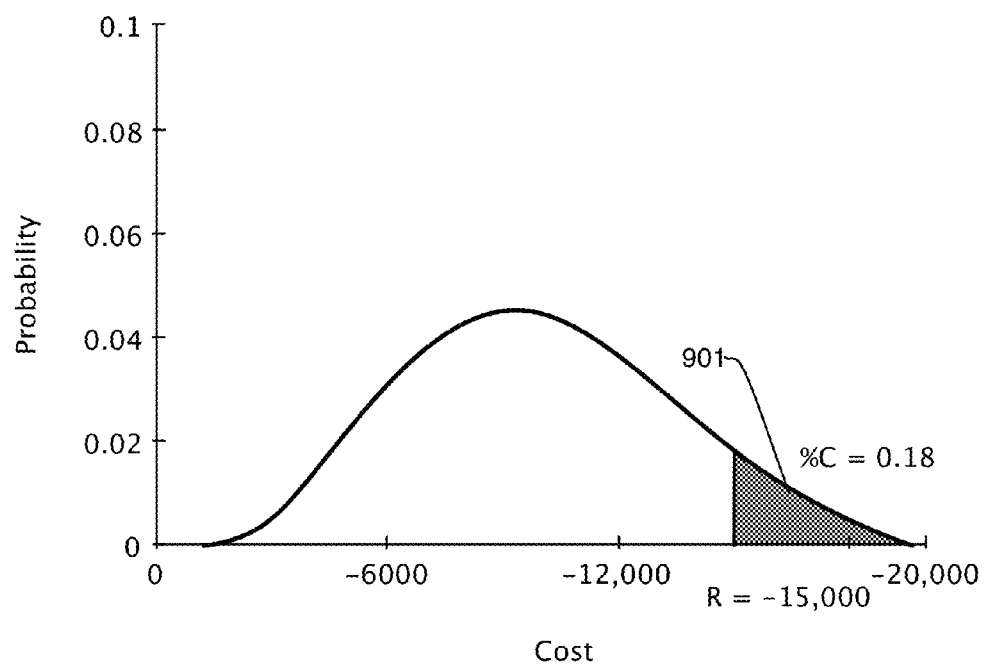
FIG. 9 is an illustrative graph of the probability distribution of costs spanning the interval from negligible costs to $20000 and the cut-off cost R=$15,000 corresponding to the cumulative probability of 18 percent.

In a percentile function the cumulative probability of the cost equal to or greater than the value of the function R is the predefined preference parameter %C. This utility function is used when the optimization of the decision involves taking into account only the costs above a threshold R whose cumulative probability is equal to %C. In FIG. 9 I show an example of the quantile function operating on the distribution of costs depicted by a bell-shaped curve, whereas the preference parameter %C=18% selects the range of costs whose cumulative probability is equal to 18%=0.18, shown as the black area 901. In this example the value of the quantile preference function is R=−$15,000.

The fourth type of the utility function, a linear function F=C is also configured in the first embodiment. Integration of this utility function over the distribution of costs gives the standard "expected" costs X(C). This linear utility function is equivalent to a CARA utility function with the tolerance parameter tending to infinity $\eta \to \infty$.

Optimization Computing Module, the Optimal Decision, and the Method of Iterations Now I will describe how the elements of the first embodiment of the invention are working together toward finding the optimal decision. I will then show the method of iterations implemented in the first embodiment. The method of iterations is applicable when the obtained optimal decision indicates that there is no sufficient quantitative reason to act.

In the first embodiment of the invention the optimization engine computing module 105 is configured to find the solution for the problem of the optimization of costs by finding the treatment T, given the evidence and the possible distribution of benefits and costs, that is most preferable according to the individual preferences of the parties involved. As I show in the FIG. 11, the evidence E is supplied by the medical evidence data entry module 101. The evidence E is passed to the computing module for the model of the disease 102. The module 102 applies the model of the disease to obtain the distribution of possible outcomes during the natural course of the disease. The module 102 outputs probability distributions of states of the disease and transitions into other states P(S|EI), P(S|EIT) for different treatments T and for the natural, or the baseline progression of the disease. These distributions are passed to the module for the model of costs 103 and benefits 104. These modules output probability distributions of costs and benefits P(C,B|EIT). The computing module for the individual preferences 106, given the distributions of costs and benefits, computes the utility functions F($\eta$, EIT) parameterized with the individual preferences $\eta$ for the patient, and for the provider—as described in the previous section.

Figure 10:
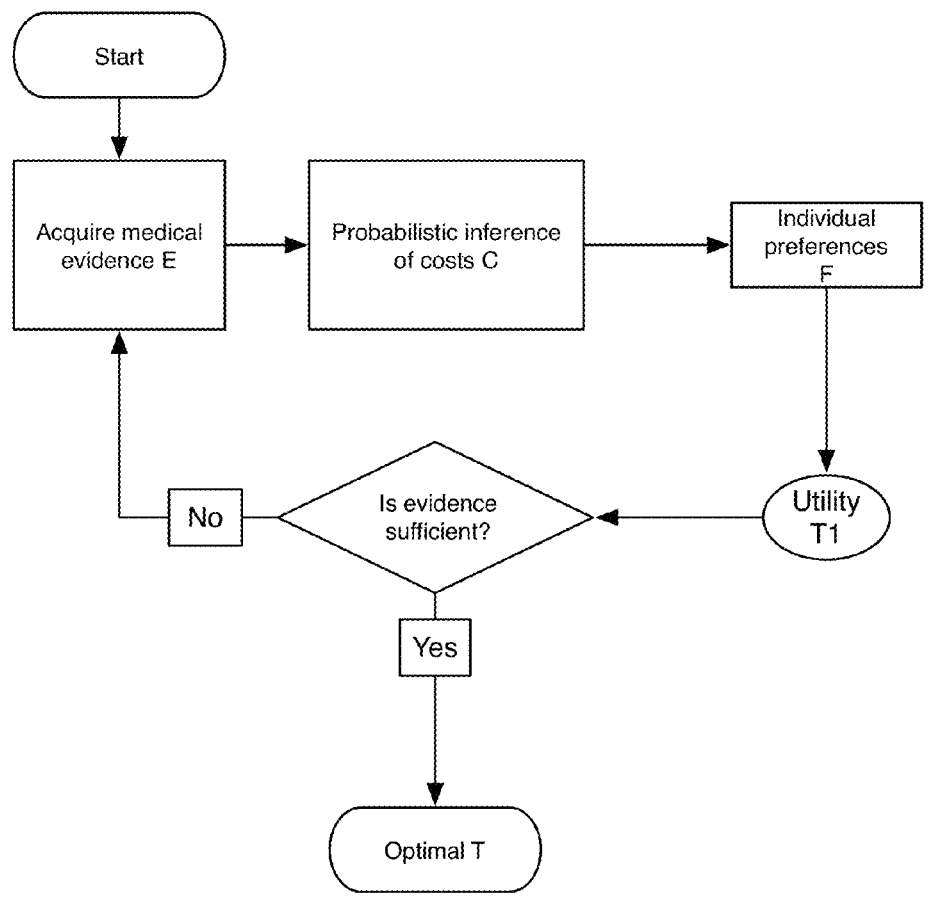
FIG. 10 is a flowchart showing the method of iterations of refining the evidence.

In FIG. 10 I show that before the optimal medical treatment is found there is a chance that the medical evidence is found insufficient to make a decision. A situation is possible when optimization results indicate that the obtained evidence is insufficient to apply any treatment. In the first embodiment this happens when the calculated utility of any treatment is lower than the baseline utility of the natural course of the disease. At this point additional evidence needs to be obtained before the system produces an optimal decision different from the baseline treatment. In the first embodiment the cost of obtaining an additional evidence is evaluated against the possible utility improvement given additional evidence, which allows the costs of obtaining evidence to be controlled in the same way as the costs associated with treatments.

When the evidence is finally sufficient to pass the intermediate decision point, the optimal medical decision T corresponding to the greatest utility is displayed to the user.

In the next section I will describe the operation of the first embodiment in concrete details using the modules and the methods described in the earlier sections.

Operation of the First Embodiment

In this section I will describe the operation of the first embodiment of the invention. First, I will describe the general operation and the method of reconciliation, followed by a concrete example of the operation of the system in the drug approval process. The description shows that the operation of the first embodiment of the invention makes at least one medical decision making process more informative, better founded, less expensive, and potentially much faster than it is now.

General Operation

The computer system and the method for making optimal medical decisions generally operates as follows.

Figure 11:
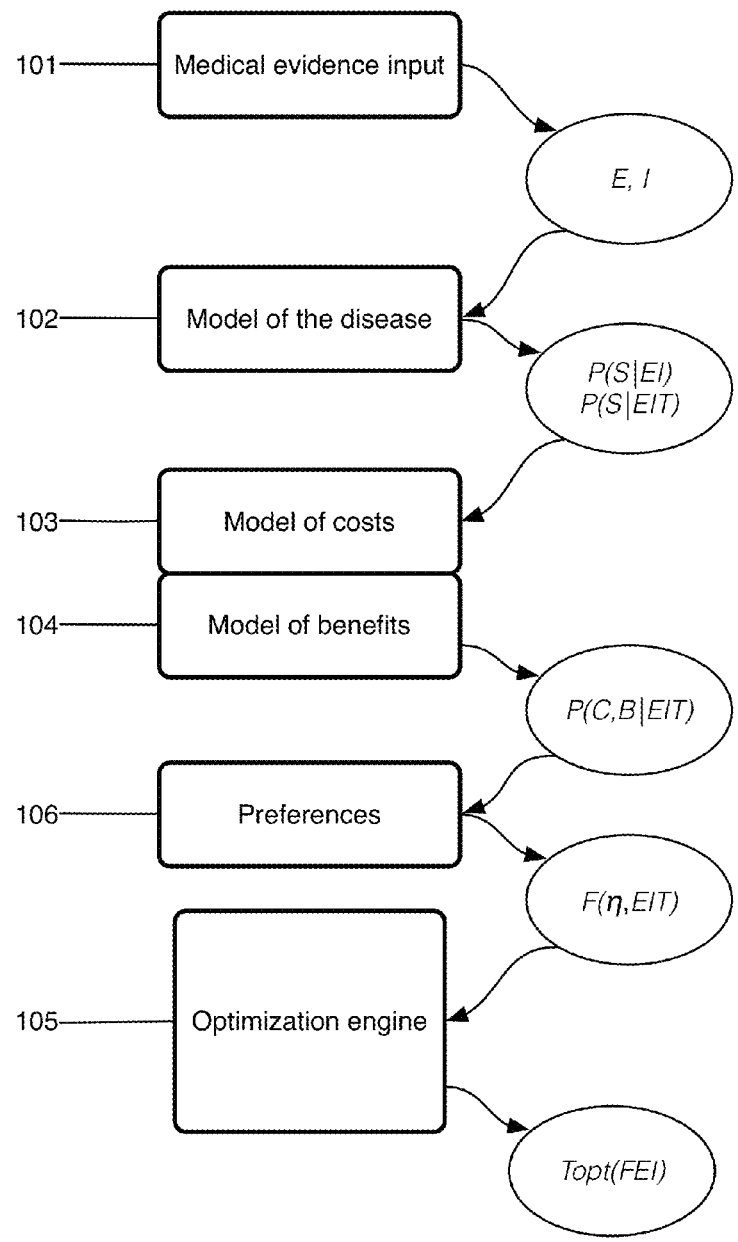
FIG. 11 is a flowchart showing the flow of data and results between the computational modules of the system of the invention.

In FIG. 11 I show that the medical evidence E comprising medical facts pertaining to the patient, and the medical opinions I, are entered into the system using the medical evidence data entry module 101. Having obtained the set of inputs E and I, the model of the disease of the module 102 produces probability distributions of the current state of the disease S, and probability distributions of future states of the disease assuming that the decision T is made and is acted upon. The patient's utility function and the individual preferences with respect to costs and benefits are entered into the system with the module 106. The provider's utility function and the preference parameters are selected with the module 106 as well. The optimization engine 105 then evaluates the expected utility values of different decisions T utilizing probability distributions produced by the module 102 and utilizing probabilistic inference of the costs and benefits with the models of the modules 103 and 104. The optimization module 105 then presents the utility values of the decisions in such a way that the decision having the greatest utility is shown as being optimal.

Method of Reconciliation

If the optimal decisions obtained by the method above for the patient and for the provider are different, they are reconciled by adjusting the patient's and the provider's utility functions. The optimization module 105 is configured to perform reconciliation by the variation of the utility functions parameters and arguments.

The optimal decision is the argument T providing the maximum of the expected utility parameterized with the tolerance parameter $\eta$, given the distribution of costs, the evidence E, opinions I and the set of treatments $\{T_i, i=1 \ldots N\}$. Denoting R the provider and A the patient, the optimal decisions are:

$$T_{oR}(\eta_R, EI) = \underset{T_i}{\mathrm{argmax}} X(F_R(\eta_R, EIT_i))$$

$$T_{oA}(\eta_A, EI) = \underset{T_i}{\mathrm{argmax}} X(F_A(\eta_A, EIT_i))$$

where X is the expectation as in the section entitled "Method for the computation of distributions of costs and of functions of costs", and the arg max notation denotes the operation of selection of such $T_i$ which provides the maximum of the argument: that is, maximum of the expectation of the utility function of the individual cost preferences.

First, the tolerance parameters are varied according to the uncertainty model $D(\eta)$ attributed to them:

$$\eta_A \sim D_A(\eta_A)$$

$$\eta_R \sim D_R(\eta_R)$$

If by varying the tolerance parameters a common optimal decision emerges, the process is stopped, the decision thus found is declared optimal for both parties and the treatment corresponding to the decision is then performed.

Otherwise, the monetary arguments of the costs and benefits are adjusted by performing hypothetical transfers. Computation of individual preferences of costs is adjusted by adding the transfer amount from the provider to the patient or vice versa: ☐ ☐

$C_A \rightarrow C_A + TR$ $C_R \rightarrow C_R - TR$

The method of transfers above is repeated iteratively until a common optimal decision emerges and the hypothetical transfers are minimal for all parties. The treatment corresponding to the optimal decision is then performed and the transfers corresponding to the optimal decision are made.

Figure 12:
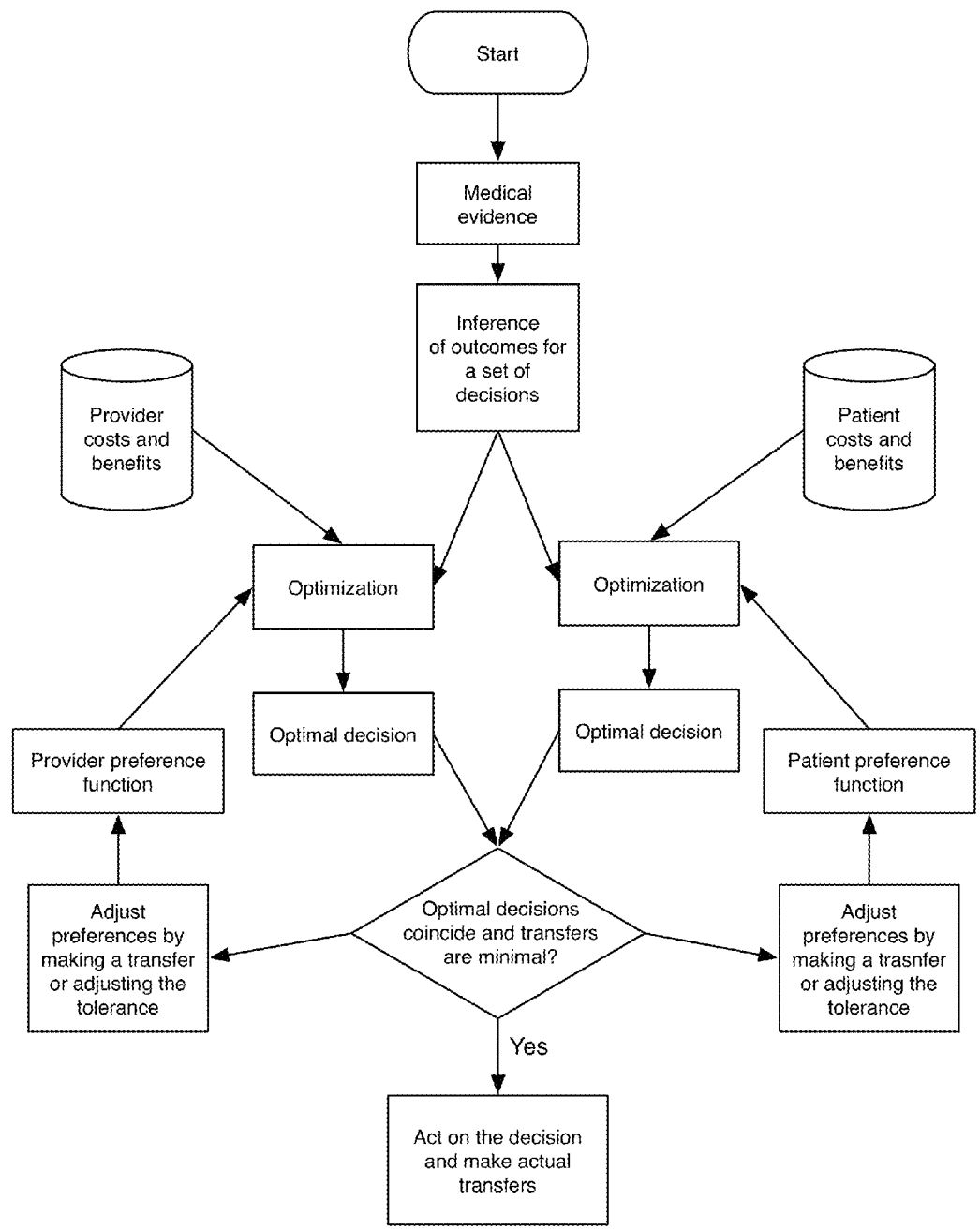
FIG. 12 is a flowchart showing the information flow during the process of reconciliation of optimal medical decisions.

In FIG. 12 the flowchart shows how the optimal decision is obtained for both the patient and the provider and then is reconciled until a common optimal decision arises.

Operation in Application to the Drug Approval Process

Now I will discuss the operation of the first embodiment in the possible application of the method and the system described in the previous sections. This use relates to the approval process of a hypothetical medical drug. A person skilled in the art recognizes that the focus on the specifics of the drug approval process is necessary only for illustrative purposes and does not limit the nature of the invention, the description of the method, or its possible applicability in any way.

A chemical treatment—a medical drug—is proposed to treat a certain type of cancer. The user of the system is to make a decision whether the drug is feasible as the treatment for a certain stage of the disease. The results of the test are represented by the list of individuals that underwent the treatment by the drug. Results of other treatments along with the continuously updated sets of evidence, treatments, and outcomes are also contained in the database.

Step 1: Data input and the initial screening. The user first inputs the evidence $E_i$ for each patient, for instance, the set of measurements of lymphatic, liver, spleen enlargement, or the direct evidence. Given the evidence, for each patient the system determines the probability of being in a certain state of the disease. In the following table the hypothetical numbers are shown.

☐ ☐ ☐

| State of the disease, given E | Description | Probability of the state : example 1 | example 2 |
|---|---|---|---|
| S0 | No disease | P0 = 0.0 | P0 = 0.01 |
| S1 | First stage | P1 = 1.0 | P1 = 0.8 |
| S2 | Second stage | P2 = 0.0 | P2 = 0.19 |
| S3 | Third stage | P3 = 0.0 | P3 = 0.0 |
| S4 | Fourth stage | P4 = 0.0 | P4 = 0.0 |
| S5 | Complications | P5 = 0.0 | P5 = 0.0 |
| SD | Death | PD = 0.0 | PD = 0.0 |

There are two examples in the table above. In the example 1, given the evidence E, it is certain that each patient has the stage 1 of the disease. In the example 2 in the table above the probability of the state S1 is P1=0.8, probability of state S2 is P2=0.19 given the evidence E, and there is a small probability P0=0.01 that there is no disease. For the purpose of the illustration let me first assume that the evidence is pointing to the stage of the disease with certainty as in the example 1 in the table above.

Step 2: Probabilistic inference of the model of the disease. The model of the natural course of the disease is stored in the system prior to the trial. The natural course of the disease is the course of the disease under no treatment, or under a standardized baseline treatment. The natural course of the disease is available as the selection item in the menu of choices presented to the user. Selection items in the menu of choices are disease-dependent. For example, since the disease in the example is a form of cancer, the baseline treatment is a standardized, common variant of chemotherapy, radiotherapy, or surgical removal of the tumor.

The natural course of the disease is modeled by the following transition matrix denoting probabilities of changing the state of the disease from one to another during the next period:

$$p_{ij} = \begin{cases} p_{00} & p_{01} & p_{02} & p_{03} & p_{04} & p_{05} & p_{0D} \\ & & & \cdots & & & \\ p_{40} & p_{41} & p_{42} & p_{43} & p_{44} & p_{45} & p_{4D} \\ & & & \cdots & & & \\ 0 & 0 & 0 & 0 & 0 & 0 & 1 \end{cases}$$

The last state SD, the state of death, is the terminal state which is indicated by the sixth row in the transition matrix above: there are no transitions from the terminal state into any other state of the disease.

Step 3: Probabilistic Inference of the model of the treatment. The treatment T with the drug under investigation results in transition probabilities differing from these in the natural course of the disease: ☐ ☐

$$p_{ij}(T) = \begin{cases} p_{00}(T) & p_{01}(T) & p_{02}(T) & \ldots & p_{0D}(T) \\ & & \cdots & & \\ p_{40}(T) & p_{41}(T) & p_{42}(T) & \ldots & p_{4D}(T) \\ & & \cdots & & \\ 0 & 0 & 0 & \ldots & 1 \end{cases}$$

Probabilities in each row of the matrix are governed by the Dirichlet distribution. Parameters of the new Dirichlet distribution are obtained using the data about the course of the disease under the proposed treatment, the new anti-cancer drug.

Step 4: Decision making Having entered the baseline model and the new model, the user of the system now computes to resolve whether the new drug is better than the baseline procedure when applied for the stage 1 of the disease. For this the user of the system selects a utility function from the set of the possible utility functions. For the purpose of illustration of the operation of the method we consider a simple linear function of the costs.

For the purposes of illustration consider costs of being in a certain stage of the disease as certain. Costs which are certain are modeled as extremely localized probabilistic distributions and in our illustration are represented simply by numbers in the following table.

| State of the disease | Description | Cost distribution, $ var. 1 | var. 2 |
|---|---|---|---|
| S0 | No disease | C0 = 0 | C0 = 0 |
| S1 | First stage | C1 = −1000 | C1 = −1000 |

-continued

| State of the disease | Description | Cost distribution, $ var. 1 | var. 2 |
|---|---|---|---|
| S2 | Second stage | C2 = −1000 | C2 = −2000 |
| S3 | Third stage | C3 = −2000 | C3 = −2000 |
| S4 | Fourth stage | C4 = −3000 | C4 = −2000 |
| S5 | Complications | C5 = −4000 | C5 = −4000 |
| SD | Death | CD = −100000 | CD = −100000 |

The transition probabilities from the stage 1 of the disease in the baseline treatment or baseline scenario and in the suggested treatment or suggested scenario are as follows:

| Transition probabilities | | | | | | | |
|---|---|---|---|---|---|---|---|
| Treatment | 1 → 0 | 1 → 1 | 1 → 2 | 1 → 3 | 1 → 4 | 1 → 5 | 1 → D |
| Baseline | 0.6 | 0.1 | 0.1 | 0.0 | 0.0 | 0.0 | 0.2 |
| Proposed T | 0.6 | 0.2 | 0.0 | 0.0 | 0.0 | 0.0 | 0.2 |

According to the user's selection of the linear utility function the expected value of the utility computed by the optimization engine is

☐

| Utility under cost distribution | | |
|---|---|---|
| Treatment | var. 1 | var. 2 |
| Baseline | −20200 | −20300 |
| Proposed Treatment T | −20200 | −20200 |

Step 5: Solution. The system now outputs the optimal decision. Given the cost distribution var. 1, there is no additional value in the treatment T. However, if the system is given the cost distribution var. 2, the additional value of the new treatment is 100 units. T is therefore superior to the baseline treatment. If the cost distribution is given by the example 2, the user of the system approves the new treatment T. The statement of approval of the new anti-cancer drug must specify the utility function parameters, the model of the disease parameters, and the parameters of the distribution of costs.

Step 6: Comparison with other solutions. By applying an alternative utility function the system also outputs the survival rates under the proposed treatment. In the example provided the user observes that while the value of the new treatment is better, the survival rates of both treatments are essentially the same. Computing the aggregate survival rate is the one of the standard methods of decision making adopted by the Federal Drug Administration in the United States of America. This and other standard methods are incorporated in the system as alternative utility functions. The statement of approval of the new anti-cancer drug specifies its standing with respect to other treatment using other utility functions, including aggregate functions such as survival rates. The statement of approval specifies that while the value of the new anti-cancer drug is greater than the value of the baseline treatment, the aggregate survival rate is not improved.

Step 7: Ramifications of the uncertainty of the state of the disease. I will now briefly consider the operation of the system in the case when the stage of the disease is uncertain. This is the example 2 in the table in the section Step 1. In this case the system computes the utility values for the baseline and for the proposed treatments given the evidence.

It is conceivable that the patients are selected based on the essential similarity of the obtained evidence. In this case the user utilizes the system of the invention to solve the problem of approval or disapproval of the new treatment for patients exhibiting this evidence. The system computes the optimal decision for a given utility function and a given set of symptoms. For this, the distribution of the costs is computed for the baseline treatment and for the proposed treatment T:

$$P(C \mid E_0) = \sum_{S_i, S_j} P(C \mid S_j) p_{j,i} P(S_i \mid E_0)$$

$$P(C \mid T, E_0) = \sum_{S_i, S_j} P(C \mid S_j) p_{j,i}(T) P(S_i \mid E_0)$$

The solution is computed by the system of the invention, as in the case of the certainty, by integrating the utility function of choice over the distribution of costs, and by further comparing the expected values for the baseline treatment and the proposed treatment. Again, several utility functions can be used, including the standard survival rates function used by the regulatory bodies.

Step 8: The method of reconciliation in the drug approval process. Risk tolerances of different groups of potential patients are entered in the decision making process. If for some groups the proposed treatment is better than the baseline treatment, the drug is approved as providing a better treatment for these groups of patients.

Note from the above description of the operation of the invention that the system uses standard probabilistic inference methods to evaluate distributions of probabilities. Unlike the aggregate quantities (averages and expectations), distributions of probabilities preserve—to the extent possible by the underlying model—all available information about the process. For this reason even a very limited amount of data is sufficient to infer helpful information about the unknown and uncertain transition probabilities. The effects of various medical decisions are quantified and the effects of the imperfect information about the disease and proposed treatments are consistently taken into account by the system of the invention. Using the system of the invention a positive or negative decision can be obtained along with the statements of possible risks much faster and at a lesser cost than a decision based on aggregate quantities. This is a significant advantage of the system in application to the medical remedy approval process.

Decision Recovery and the Rollback Mechanism

I will now describe the mechanism by which the computing systems of the invention are capable of reproducing past optimal medical decisions.

The computing systems on which all the models reside are capable of engaging the models as of a certain date.

The model as of a certain date includes all the medical facts and the data, and all the models based on these facts and data available at a specific date in the past. The previous state of the model is therefore not erased and is recoverable at any point of time. For example, the model as of a certain date contains the parameters of the probabilistic distribution known at that date: the model represents the probability of a medical condition given all the medical evidence available at that date.

Figure 6:
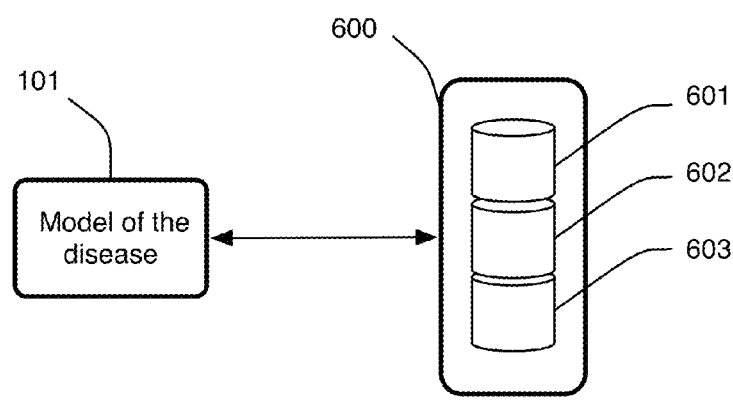
FIG. 6 is a scheme showing that the model of the disease is connected to the data storage configured to provide the "as of date" functionality.

A special software rollback mechanism ensures that the model can be restored. In the first embodiment of this invention the rollback software mechanism provides periodic snapshots of the model. In FIG. 6 I show the computing system on which a model resides connected to a database 600, comprising three snapshots of the model data 601, 602, and 603 corresponding to three distinct dates. In the first embodiment of the invention the frequency of snapshots depends on the rate of innovation of the disease-specific and the treatment-specific models and data in the database. Methods of probabilistic inference are capable of incorporating a single datum as well as batches of data. The first embodiment under normal conditions is supplied with weekly and monthly updates of its models. In abnormal conditions, however, such as rapidly developing epidemic, or a military operation, frequent updates of the models are necessary. For this reason the first embodiment is capable of both single-datum and batch updates and snapshots of the models are taken after every update.

When recovery of the decision making process is requested by the user, the corresponding snapshot is retrieved from the database 600. The models are thus rolled back to the state in which they existed at the specified date. The system is then supplied with evidence and the decision process is performed. The optimal decision thus obtained corresponds to the optimal decision which would have been made on the date specified.

The model recovery via the rollback mechanism allows the user at any point in time to reproduce the optimal decision which have been made, or would have been made at any point in the past. This is an objective and impartial way to replicate the decision making process leading to optimal medical decisions. For this reason it is invaluable in legal disputes, in regulatory investigations, and in all other cases necessitating a posterior judgement about medical decisions.

ADVANTAGES

From the above description the reader can see that some embodiments of the medical decision making system and its operation have several advantages differentiating it from the traditional process of making medical decision:

- The system is configured to be able to use all available clinical data in the form of probabilistic models of diseases. It is therefore more informative than the traditional decision making process which operates with aggregate quantities like averages and expectations (average survival rate, average recovery rate). The methods of the first embodiment accounts for the fact that all models are imprecise. It is thus much more reliable. The first embodiment uses probabilistic inference to evaluate distributions of probabilities. Distributions of probabilities preserve—to the extent possible by the underlying model—all available information about the process. For this reason even a limited amount of data is sufficient to infer helpful information about the uncertain course of the disease and about the uncertain effects of treatments on it.
- The system is configured to incorporate opinions or beliefs in the decision making process. Opinions or beliefs are incorporated in the form of the parameters of the models, for example, parameters of prior probability distributions, and in the form of cost and benefit preferences. Opinions and beliefs thus incorporated can represent the body of knowledge, personal experience, and risk preferences of doctors, providers of medical services, patients and other parties affected by the process of the medical decision making
- The system of the invention is configured to incorporate costs models at different stages of the disease. The costs are variable and the cost models are imprecise. Utility values associated with them are different for different patients. The cost of the treatment can be different for different providers. For this reason the system finds such optimal medical decision which is mostly suitable for the patient's and the provider's particular situation and their circumstances. This feature of the first embodiment opens the possibility of an intelligent, informed design of patient-specific therapies. At least one embodiment of the system facilitates quantifying benefits and costs associated with patient-specific or group-specific medical drugs, therapies and remedies. This opens the possibility of developing patient-specific and group-specific treatments at a significantly lower cost compared to the current system where the new therapy, drug or remedy must benefit and be safe for every potential patient.
- The invention is configured to re-evaluate decisions made in the past. In the case of a dispute the system can reproduce the whole decision making process as if it were done at a specific date (the "as of" date functionality of the first embodiment) to confirm or to deny that the disputed decision has been made using all the data and all the circumstances available at the time of the decision making.

The invention thus represents an advantageous system and method of making medical decisions. It consistently takes into account costs and benefits of the treatment and optimizes these costs based on quantitative data and models of the disease.

It permits individual evaluation of the value of prospective and existing drugs, remedies and therapies. Currently the health care regulations are based on aggregate quantities and are meant to protect and ensure the existence of benefits for the whole population. The excessive protection results in excessive cost borne by all pharmaceutical companies. The companies must expend efforts to make sure that the medical drugs and remedies are safe and effective for the whole population. This regulatory regime places excessive resource burden on small companies and thus severely restricts innovation in health care. From the above description the reader sees that at least one embodiment of the invention opens the possibility of reducing the burden of regulations in the medical industry. The system and the method of the invention permits objective, informed, data-based and commonly adopted model-based decision that will make more treatments available for specific groups or even for individual patients.

CONCLUSIONS, RAMIFICATIONS AND SCOPE

Accordingly, the reader will see that various embodiments of the optimal medical decision making system can be used. They all achieve the goal of the invention to make the medical decision process significantly more informed, decisions—quantitatively justified and fair, and less expensive in their implementation.

While the detailed description contains many specific elements and methods, they must not be regarded as limitations of the scope of the invention, but as the specific elements and methods of the first embodiment. Many other embodiments are possible.

In the first embodiment of the invention the model of the disease is presented by a matrix of transition probabilities. More complex models, such as those represented by Bayesian networks or hidden Markov models, which include many interconnected nodes or stages of the disease, are possible in other embodiments of the invention. Other embodiments of the invention are configured to utilize these and other models which are capable of evaluating probabilities of distinct states of the disease and probabilities of different diseases based on medical evidence. Increasing complexity of models in other embodiments may lead to a better prediction of the course of the disease. More complex models of the disease may improve the efficiency of the system when and where this rectification is cost-effective.

In other embodiments the model of costs and benefits are represented by dynamic programming models. Such dynamic models shall consider the possibility of several consecutive medical treatments and their consequences on the next stage, on the stage following the next stage, etc., or on the whole course of the disease. Other embodiments of the invention are configured to utilize these and other complex models capable of evaluating probabilities of costs and benefits.

For long and chronic diseases the time value of monetary or non-monetary units of measurement of costs and benefits becomes important. Other embodiments of the invention incorporate combined account of all possible future costs and benefits as the sum of their discounted values.

Other embodiments of the invention are configured to include other functional forms linking individual preferences with costs and benefits. These more complex forms are represented by a vector of utility functions, or by a linear or non-linear combination of costs and benefits. Cost and benefits in other embodiments include those accrued during all future stages of the disease.

In other embodiments different models of uncertainties are configured in addition to the distributions configured in the first embodiment (Dirichlet, Beta, binomial distributions etc).

Methods of integration and summation over costs and parameters of models in other embodiments include numerical simulations, Monte Carlo methods, Markov Chain simulations, and other techniques deemed to be efficient in evaluating predictive quantities in problems involving uncertainty of models and data.

Optimization and decision making in other embodiments can involve, for example, a computer-assisted selection by a user (a doctor, or a nurse, or the patient), or, for example, a fully automated selection of the optimal treatment.

In other embodiments operation of the system can be fully automated and respond to the changing situation in real-time. The system can be connected to a device administering a drug or another remedy to the patient in a fully automated way.

Accordingly, the scope of the invention should be determined by the appended claims and their legal equivalents, rather than by the specific examples given.

I claim:

1. A method of making optimal medical decisions, comprising:
   (a) collecting a medical evidence about a patient comprising standardized medical facts,
   (b) providing a model of the evidence linking said medical evidence with a set of probable current states of the disease,
   (c) providing a model of the progression of the disease linking each of said probable current states of the disease with a set of probable future states of the disease,
   (d) providing a model of the progression of the disease linking probable current states of the disease with the probable future states of the disease for a plurality of medical decisions,
   (e) providing a model of costs and benefits associating a set of probable costs and benefits along with their probabilities for each of said probable current states of the disease, and for each of said probable future states of the disease,
   (f) providing a preference function of costs and benefits outputting a utility value for a combination of costs and benefits approximately reflecting real individual preferences of said combination of costs and benefits,
   (g) generating an expected utility value by summing the values of said preference function of costs and benefits weighted with probabilities of costs and benefits for each of said medical decisions,
   (h) selecting a resulting medical decision having the largest expected utility value,
   whereby said medical decision will be approximately optimal with respect to the expected progression of the disease, and with respect to costs and benefits, and with respect to individual preferences.

2. The method of making optimal medical decisions of claim 1, wherein said model of the evidence is a probabilistic inference model comprising:
   (a) establishing a set of distinct types of evidence,
   (b) establishing a plurality of states of the disease,
   (c) collecting a set of medical data comprising clinical observations of said distinct types of evidence and said states of the disease,
   (d) collecting opinions of medical professionals comprising approximate likelihood of said states of the disease given said distinct types of evidence,
   (e) establishing a probability distribution approximately describing probabilities of said states of the disease given said distinct types of evidence, said probability distribution comprising a functional form and a set of model parameters,
   (f) computing using probabilistic inference the values of said set of model parameters from said set of medical data and said opinions,
   (g) calculating said probabilities of said states of the disease given said distinct types of evidence on request,
   whereby said probabilistic inference model represents the body of information inferred from clinical observations and opinions of medical professionals in a functional and parametric form convenient for further inference and automated decision making.

3. The method of making optimal medical decisions of claim 1, wherein said model of the progression of the disease is a probabilistic chain comprising:
   (a) establishing a plurality of medical states,
   (b) establishing a set of treatments,
   (c) collecting a set of medical data comprising clinical observations of transitions between said medical states given each of said treatments,
   (d) collecting opinions of medical professionals comprising approximate likelihood of transitions between said medical states given each of said treatments,
   (e) establishing a probability distribution approximately describing probabilities of transitions between said medical states given each of said treatments, said probability distribution comprising a functional form and a set of model parameters, (f) computing using probabilistic inference the values of said set of model parameters from said set of medical data and said opinions, (g) calculating said probabilities of transitions on request, whereby said probabilistic chain represents the body of information about the progression of the disease inferred from clinical observations and opinions of medical professionals in a functional and parametric form convenient for further inference and automated decision making.

4. The method of making optimal medical decisions of claim 1, wherein said probabilistic chain is a Markov chain, comprising a probability distribution matrix wherein said probabilities of transitions between said medical states depend only on the probable current medical state and the probable future medical state.

5. The method of making optimal medical decisions of claim 1, wherein said model of costs and benefits is a probabilistic model of costs and benefits comprising:

(a) collecting clinical data and opinions regarding costs associated with the probable state of the disease, and data on benefits of treatments, (b) establishing a probabilistic model of costs and benefits in the form allowing for predictive inference comprising lookup tables and parameterized functions, (c) computing using probabilistic inference the values of parameters of said parameterized functions, (d) populating said lookup tables, (e) calculating probability of costs and benefits on request, whereby said model of costs and benefits represents the body of information about probable costs and benefits in the form suitable for further inference and automated decision making.

6. The method of making optimal medical decisions of claim 1, wherein said preference function of costs and benefits is a function of costs, benefits and parameters representing approximate value of the combination of costs and benefits for the patient.

7. The method of making optimal medical decisions of claim 1, wherein said preference function of costs and benefits is a function of costs, benefits and parameters representing approximate value of the combination of costs and benefits for the provider of medical care.

8. The method of making optimal medical decisions of claim 1, wherein said probability distributions of costs and benefits are functions of non-monetary costs and of non-monetary benefits.

9. The method of making optimal medical decisions of claim 1, wherein said probability distributions of costs and benefits are functions of monetary costs and of monetary benefits.

10. A computer system for making optimal medical decisions, comprising:

(a) a data input means for collecting, storing, and outputting medical evidence, (b) first computing processor means for operating a model of evidence configured to receive said medical evidence from said data input means, to retrieve the model of evidence from the data storage, to infer probable current medical states given said medical evidence, and to store and forward the output, (c) second computing processor means for operating a model of the progression of the disease configured to retrieve said model of the progression of the disease from the data storage, to infer, given possible medical decisions, probable future medical states from the probable current medical states, and to store and forward the output, (d) third computing processor means for operating a plurality of models of costs and benefits configured to retrieve said models of costs and benefits from the data storage, to infer, given possible medical decision, probable costs and benefits for each of said probable future medical states, and to store and forward the output, (e) fourth computing processor means for operating personal preference functions configured to accept a formula and a set of parameters from approximately reflecting the circumstances and preferences of the user of the system, to calculate an approximate value for the user of each combination of costs and benefits, and to store and forward the output, (f) fifth computer processor means for evaluation and optimization of costs and benefits of said medical decisions configured to compute preference values of said personal preference functions for the probable costs and benefits, to rank said preference values, to display the medical decision corresponding to the highest preference value as said optimal medical decision, to process the optimal decision, and to store and forward the optimal decision.

11. The computer system for making optimal medical decisions of claim 10, wherein said data input means for collecting, storing, and outputting a medical evidence comprises automated data collection means for supplying the medical evidence in realtime.

12. The computer system for making optimal medical decisions of claim 10, further including technical means for automated delivery to the patient of the optimal treatment specified in the optimal decision.

13. A method for making optimal medical decisions, comprising:

(a) collecting a plurality of medical evidence data, (b) establishing approximate probabilities of a plurality of distinct states of the disease compatible with said medical evidence data, (c) establishing approximate probabilities of a plurality of future distinct states of the disease for a plurality of medical treatments, (d) establishing probabilities of costs and benefits for each of the future distinct states of the disease and probabilities of costs of said medical treatments, (e) establishing a utility function operating over said costs and benefits each combination of costs and benefits, (f) computing an expected utility function over the probabilities of costs and benefits of future states of the disease and over the probabilities of costs of each of said medical treatments, (g) sorting said medical treatments by the value of said expected utility function, (h) selecting the medical treatment corresponding to the top value for said expected utility function, whereby the medical treatment selected in the last step is the optimal medical decision.

14. The method for making optimal medical decisions of claim 13, wherein said probabilities of said plurality of distinct states of the disease are computed from said plurality of collected medical evidence using probabilistic inference.

15. The method for making optimal medical decisions of claim 13, wherein said probabilities of a plurality of future distinct states of the disease are computed from said plurality of proposed medical treatments using probabilistic inference.

16. The method for making optimal medical decisions of claim 13, wherein the probabilities are represented by a plurality of model distributions which further include uncertainty of said models.

17. The method for making optimal medical decisions of claim 13 further including
- (a) establishing a patient utility function approximately representing utility preferences of the patient
- (b) establishing a provider utility function approximately representing utility preferences of the medical care provider,
- (c) selecting a patient optimal medical decision corresponding to said patient utility function,
- (d) selecting a provider optimal medical decision corresponding to said provider utility function,
- (e) comparing said patient optimal medical decision and said provider optimal medical decision,
- (f) modifying arguments and parameters of said provider utility function and said patient utility function if said provider optimal medical decision and said patient optimal medical decision are not substantially the same,
- (g) establishing an iterative process in which last three steps until said provider optimal medical decision and said patient optimal medical decision are substantially the same and said iterative process stops, whereby the optimal medical decision obtained is common for the patient and for the medical care provider.

18. The method for making optimal medical decisions of claim 17, wherein said iterative process further includes adjusting arguments of the utility functions by including monetary transfers.

19. The method for making optimal medical decisions of claim 18, wherein said iterative process further includes decreasing said monetary transfers while preserving the commonality of the optimal decisions, until said monetary transfers are minimal.

* * * * *